United States Patent [19]

Mangialardi, Jr. et al.

[11] 4,068,167
[45] Jan. 10, 1978

[54] RADIAL ELECTRODE FOR DETERMINING THE AMOUNT OF MOISTURE IN SEED COTTON

[75] Inventors: Gino J. Mangialardi, Jr., Greenville; Anselm C. Griffin, Jr., Leland, both of Miss.

[73] Assignee: The United States of America as represented by the Secretary of Agriculture, Washington, D.C.

[21] Appl. No.: 719,870

[22] Filed: Sept. 1, 1976

[51] Int. Cl.² ............................................. G01R 27/02
[52] U.S. Cl. .................................................. 324/65 P
[58] Field of Search .......................... 324/65 R, 65 P

[56] References Cited

U.S. PATENT DOCUMENTS

| 2,528,342 | 10/1950 | Cuckler | 324/65 R X |
|---|---|---|---|
| 2,542,331 | 2/1951 | Hiensch | 324/65 R X |
| 2,653,298 | 9/1953 | McKinley | 324/65 R |
| 2,659,048 | 11/1953 | Zabel et al. | 324/65 R |
| 2,852,740 | 9/1958 | Posey et al. | 324/65 R |
| 2,870,405 | 1/1959 | Wright et al. | 324/65 R |
| 3,035,226 | 5/1962 | Strandberg | 324/65 R |
| 3,384,815 | 5/1968 | Lyall et al. | 324/65 R |
| 3,541,437 | 11/1970 | Karl-Heinzahrweiler | 324/65 R |

*Primary Examiner*—Stanley T. Krawczewicz
*Attorney, Agent, or Firm*—M. Howard Silverstein; David G. McConnell; Salvador J. Cangemi

[57] ABSTRACT

A unique radial electrode has been designed in the same configuration as the feed roller of a cotton ginning system. The electrode is then installed as part of a feed roller and properly insulated from the ginning system. When seed cotton is fed between the feed rollers the charged radial electrode becomes a signal electrode communicating with the rest of the system which forms as a ground. The resultant current flow between the electrode and the ground passing through the seed cotton produces a measure of the moisture in the seed cotton.

16 Claims, 5 Drawing Figures

RADIAL ELECTRODE FOR DETERMINING THE AMOUNT OF MOISTURE IN SEED COTTON

BACKGROUND OF THE INVENTION

1. Field of the Invention

This invention relates to an apparatus for measuring moisture in seed cotton passing through a conventional cotton ginning system. More specifically, the invention relates to a radial electrode designed, in the same configuration as a feed roller and installed as part of a feed roller of a cotton ginning system. Even more specifically, the radial electrode is insulated from the rest of the system thus forming a signal and a ground. The resultant current flow between the electrode and the ground when properly calibrated produces an accurate measure of the moisture content of the cotton passing between the said feed rollers.

2. Description of the Prior Art

It is common knowledge that many factors may affect the resistance of certain materials such as cotton to electric current flow. The factors include (1) moisture content of the material, (2) bulk density of the material, (3) impurities on the cotton, and (4) electrical path length.

The continuous measure of the moisture content in seed cotton passing through a cotton gin has always been a desirable goal in the ginning industry.

The continuous measure of moisture content in seed cotton could thus result in the beneficial effect of being able to effectively control the moisture content of cotton throughout its flow in the gin. Therefore, the moisture measurement should be made early in the ginning system. The first convenient place in modern cotton gins where the measure can be made is at the automatic bulk feed controller, although other locations such as the extractor-feeders are also convenient locations for making cotton moisture measurements.

The principal function of the automatic bulk feed controller is to meter seed cotton into the ginning system at a rate selected by the ginner. Regardless of the ginning rate, which also is the bulk cotton feeding rate, the quantity of cotton between the feed rollers at any instant is constant. Therefore, by using the feed rollers as rotating electrodes, we obtain a site where, so long as cotton is being metered into the ginning system, the bulk density of the cotton is relatively constant.

The feed rollers in the bulk feed control are radial or star-shaped and are usually 3 to 5 inches apart tip-to-tip. To overcome the variations in electrical path length that would naturally occur with different feed-roller spacing or as the roller electrodes rotate, the notion of including both the signal electrodes and ground separated by insulated spacer disks, into one feed roller was conceived so that path length is now constant and is the distance between adjacent electrodes which is fixed by the thickness of the insulated spacer.

Another major problem found in conventional systems is the short circuiting caused by cotton and trash collecting between electrodes and hopper wall. This is overcome in the instant invention by confining the signal electrode portion of the roller-electrode toward the center of the roller and the grounded portion of the roller-electrode to the ends of the roller. This is accomplished by wiring the electrode internally during construction and bringing a lead wire from the signal electrode through a hole or slot in the shaft to an insulated fitting outside the container wall. By this method insulated shaft bearings are not required and a source of faulty signal is eliminated.

It is the unique design of the instant invention for the radial electrode ("signal" electrode) to be constructed in the same configuration as the feed roller and be installed as part of the standard star-shaped steel feed rollers located in the master feed-control hopper. It must make intimate contact with cotton as it enters the seed-cotton processing system. The electrode being designed to have the same configuration as the feed rollers is mounted as a separate insulated section in the center of one of the feed rollers. This electrode is plated with layers of copper, nickel, and chrome, in that order, to prevent oxidation and to minimize the tendency of cotton to cling to it.

The signal electrode is insulated from the shaft and side sections of the feed roller by acrylic plastic mounts to which the electrode is attached by aluminum bolts threaded into vertical and horizontal portions of the mounts; the side sections of the feed roller are attached to the mounts in like manner. The electrode is 7 inches in diameter and 7 inches long; the acrylic plastic insulator between the electrode and the remainder of the feed roller is 0.75 inches wide. An insulated wire passing through the hollow roller electrically connects the electrode to a bronze fitting at the end of the shaft, where a carbon brush assembly connects the electrode system to the moisture-measuring instrument.

A companion counterrotating feed roller provides a bearing surface against which the electrode roller works to maintain a relatively constant pressure on cotton passing between them. The electrical resistance circuit extends from the signal electrode through the cotton mass to the grounded companion roller, and simultaneously to the side sections of the electrode roller that are at ground potential.

A commercial moisture detector used to measure the electrical resistance of seed cotton passing between the two electrodes reported the electrical resistance as a 0- to 10-millivolt output. This was transmitted to a chart recorded graduated as a 0 to 100 division scale and calibrated to correspond to electrical resistance.

Calibration and performance were established during development as follows:

The radial-electrode system was calibrated to measure both seed-cotton and fiber moisture. Twenty-three bales of cotton representing a wide range of moisture contents were used to establish the calibration. This cotton was harvested by spindle pickers and contained foreign matter typically present in normal cotton production. Moisture-content levels were varied by monitoring ambient relative humidity in the field and harvesting at selected periods, and by controlling the amount of water applied to the cotton harvester spindles.

During calibration the processing rate of seed cotton averaged three bales per hour. The feeder electrodes turned at 1 revolution per minute, giving a mean density of 9.6 pounds per cubic foot for seed cotton passing between the electrodes. The height of cotton in the hopper was maintained at about 4 feet by means of a conventional automatic overflow control switch.

Cotton moisture was quantitated in samples collected as cotton passed through the feed rollers and in lint obtained by hand ginning portions of the seed-cotton sample. The moisture range of seed cotton from the 23 bales was 6.7 to 17.2%. The equivalent moisture range for fiber was 5.2 to 9.2%. Moisture levels higher or lower than these were not necessary because a fiber moisture level of 5.2% is too low and 9.2% is too high for proper ginning; at these levels the detector would indicate a need for remedial action.

Precision instruments were used to calibrate the electrical resistance across the instrument input terminals and its millivoltage response. By means of appropriate equations, the actual electrical resistance of the cotton between the electrodes was converted to equivalent moisture contents of seed cotton or lint. Regression analyses of the data were used to determine the average linear relationship of the amount of cotton moisture to electrical resistance. These data are valid only for the electrode system described here, but they show that the rate of change of moisture content with change in electrical resistance is greater for seed cotton than for cotton fibers and can be used to satisfactorily control gin driers.

During a 3-year period more than 800 bales of cotton passed through the radial-electrode feed rollers with no mechanical or electrical problems.

In conjunction with studies on cotton drying and moisture restoration, the system has also been used to automatically select alternate drying routes through experimental driers based on the cotton's need for drying, and to activate the moisture restoration apparatus when the detector indicates a cotton moisture content too low for proper ginning. This was accomplished by installing cam-operated electric switches on the pen motor hub of the recorder.

The drying phase employed two 24-shelf tower driers for which the total exposure period could be varied from 8 to 20 seconds by selecting 4 drying path combinations. Damp cotton at the input feed controller requiring more than one stage of drying was automatically routed to the first drier and then to the finishing drier. Cotton requiring only one stage of drying or less than a full drier automatically bypassed the first drier and was routed through all or part of the second drier.

The route change valve above the first drier routed cotton through 24 shelves of drier No. 1 when the detector measured seed-cotton moisture at 14.5% or more; this corresponds to 90 divisions of the recorder chart scale. Seed cotton containing less than 14.5% moisture passed through the bottom shelf of tower drier No. 1 and was routed through the 1-, 13-, or 24-shelf drying path of drier No. 2.

When the detector measured seed-cotton moisture at 7.5% or less (this corresponds to 10 divisions of the recorder chart scale), humid air was directed through a feeder chute where the air mixed with the seed cotton, enabling fibers to absorb moisture. When seed-cotton moisture was more than 7.5%, the humid air bypassed the chute and was exhausted outside the gin plant. The feeder chute was located between distributor and extractor feeder and required no special routing of cotton.

Misting nozzles were later installed in the conveyor-distributor to add greater amounts of moisture to the low-moisture cottons. These are activated automatically in conjunction with the humid air subsystem. The need for quality control of cotton during ginning prompts the continuation of this work.

SUMMARY AND OBJECTS OF THE INVENTION:

The instant invention discloses a unique apparatus for continuously measuring moisture content in seed cotton being processed through a cotton gin comprising in combination an electrical signal communication with a ground which is insulated from the signal thus translating a representative reading of the moisture content in the cotton being processed.

It is the primary object of the invention to continuously measure the moisture content of cotton in a ginning operation.

It is a second object of the invention to measure the moisture content of seed cotton in a ginning operation by means of a measured electrical signal.

It is another object of the invention to use a radial electrode configurated in the shape of a ginning roller to measure the moisture content of cotton.

It is another object of the invention to install the signal electrode in the middle of the existing gin roller system.

It is another object of the invention to insulate the signal electrode from the ends of said ginning roller and use the ends as a ground.

It is another object of the invention to use other parallel rollers in the ginning system as a ground to measure the moisture content.

It is another object of the invention to use the chute or hopper as a ground to measure the moisture content.

It is another object of the invention to eliminate variations in the measured signal thus achieving accurate moisture measuring results.

It is another object of the invention to regulate or control automatically the cotton moisture conditioning process in cotton ginneries.

It is another object of the invention to eliminate errors in the measured signal due to short circuits caused by cotton or trash collecting between electrodes and hopper wall.

It is another object of the invention to measure the average moisture content of seed cotton rather than localized damp spots.

It is another object of the invention to measure moisture content of seed cotton at constant cotton density.

It is another object of the invention to automatically control the drying system of the gin.

It is another object of the invention to automatically control the moisture restoration processes.

It is another object of the invention to continuously measure the electrical resistance of metered seed cotton across a constant path length.

DESCRIPTION OF THE PREFERRED EMBODIMENTS

Figure 1:
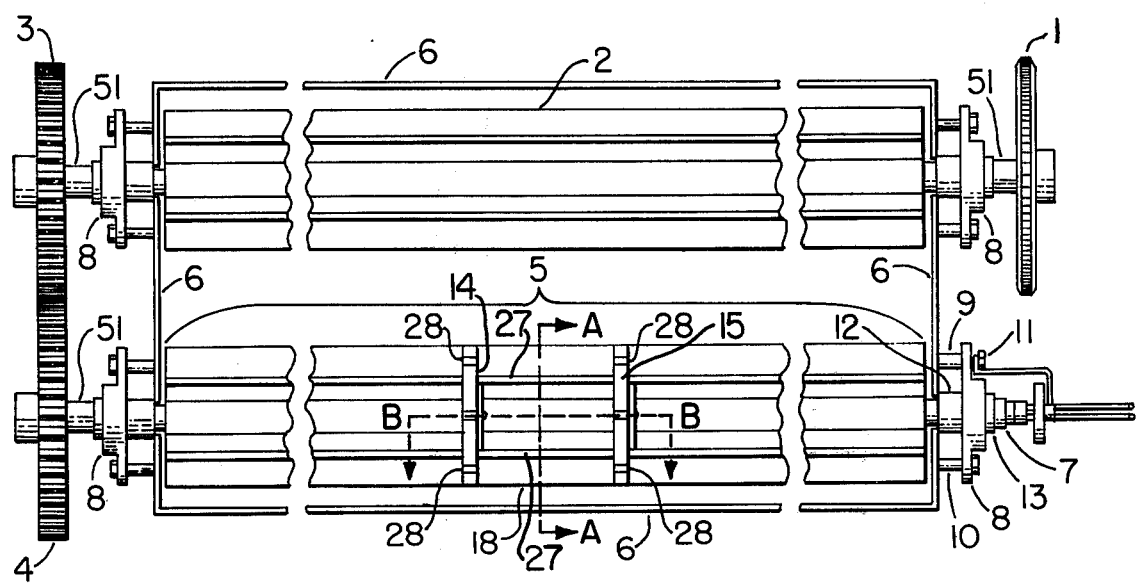
FIG. 1 shows the general location and arrangement of the signal electrode in relation to the rollers and the hopper or chute as well as the driving mechanism.

Referring now to FIG. 1 in which sprocket 1 is chain driven by a low-power variable speed drive (not shown). Sprocket 1 serves as the drive means for feed roller 2. Feed roller 2 is hollow with shafts 51 connected to the end sections and supported by rolling-contact bearings 8. Spur gear 3, which is keyed to its shaft 51, meshes with spur gear 4 and rotates measuring electrode roller 5 in a direction counter to the rotation of feed roller 2. This action feeds seed cotton between rollers and from hopper or chute 6. Spur gear 4 is keyed to its shaft. Measuring electrode roller 5 is of a construction similar to feed roller 2. That is, the roller is hollow with the end sections connected to shafts which are supported by rolling-contact bearings 8, and is of the same configuration as feed roller 2 and installed in the middle of a feed roller parallel to feed roller 2.

Spacer parts similar to 9 and 10 are welded to hopper wall 6 and serve as a base for bolting on bearings 8. Bearings 8 are held by volts 11. Collers 12 and 13 operate in conjunction with bearings 8 and maintain proper positioning along the shafts.

Shaped disks 14 and 15 (FIG. 2) are non-conducting sections which insulate the signal electrodes from the ground and eliminate current leakage between the signal and ground. A plurality of screw type fasteners 16 and 17 attach signal electrode 18 to the vertical sections of insulated disks 14 and 15 and a plurality of connectors 19 and 20 tie signal electrode 18 to horizontal sections of disks 14 and 15. Grounded roller sections 21 and 22 are connected to vertical sections of insulating disks 14 and 15 by a plurality of screw connectors 23 and 24, and are connected to horizontal sections of disks 14 and 15 by a plurality of connectors 25 and 26. Thus ground sections 21 and 22 effectively form the ends of the electrode roller 5.

Figure 2:
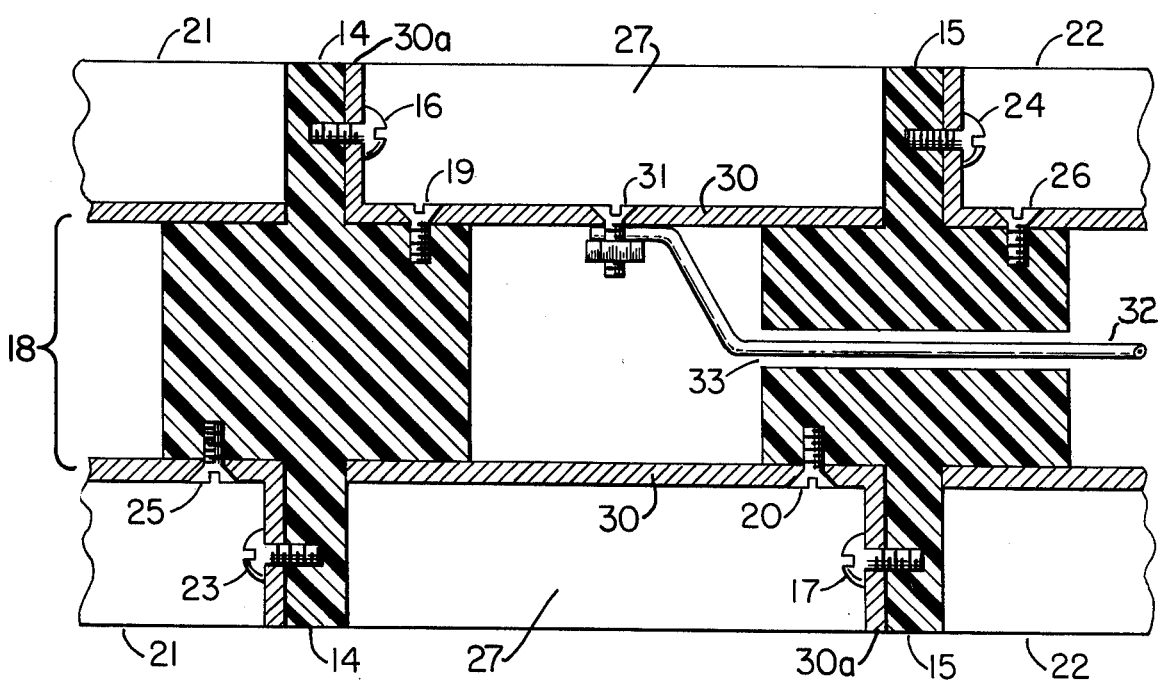
FIG. 2 (Section B) is a horizontal cross-section taken along the length of the signal electrode portion of the feed roller.
Figure 3:
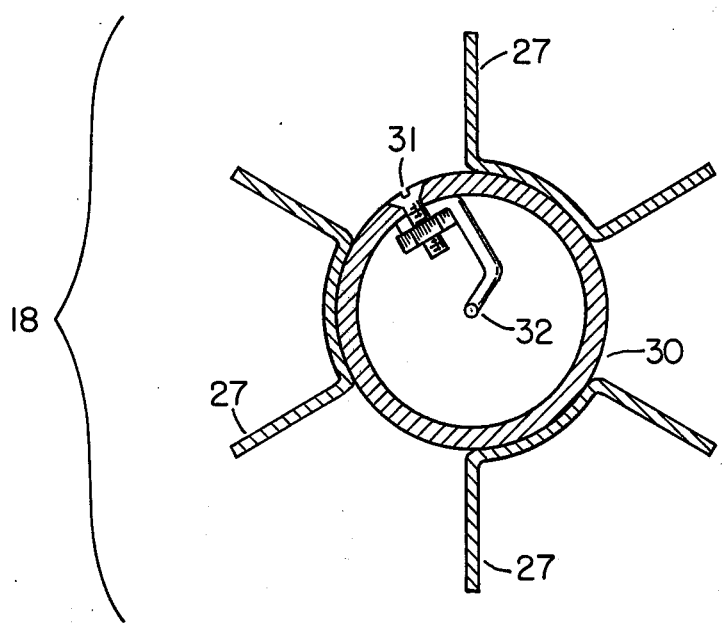
FIG. 3 (Section A) is a vertical cross-section taken through the middle of the signal electrode portion of the feed roller and describes the channel attachment to the conduit not including insulating disks.
Figure 5:
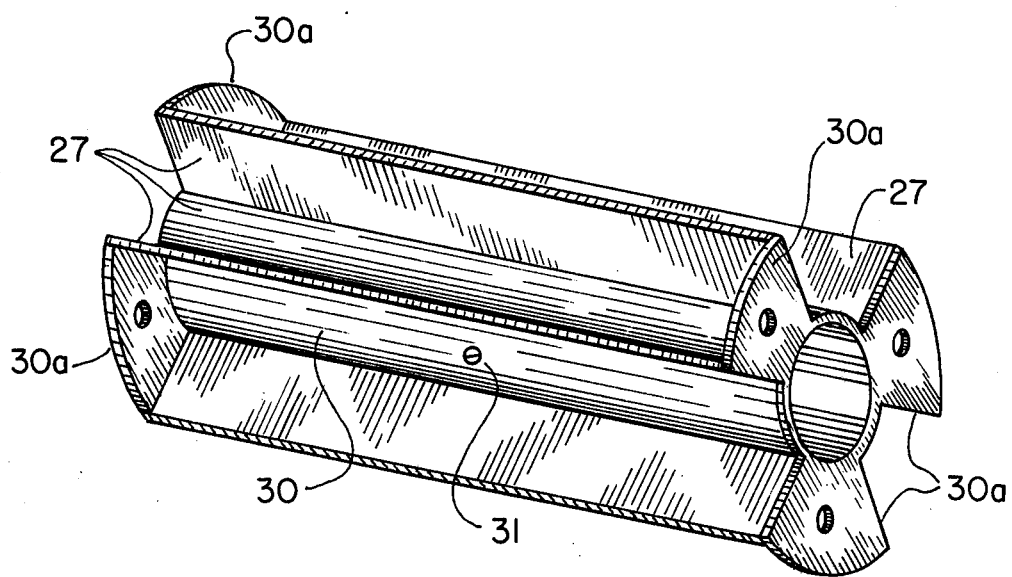
FIG. 5 is an abbreviated perspective view of the star-shaped signal electrode.

The star-shaped signal electrode shown in FIG. 3 (Section A) is constructed by welding or attaching a plurality of channel bars 27 to conduit 30. There are three spaced-apart, flange-like segments at each end of conduit 30. Present FIG. 2 shows one of such segments 30a (see FIG. 5), secured to disk 14 by screw 16. The other two flange-like segments which are at the same end of conduit 30 are hidden. FIG. 2 also shows one of such flange-like segments at the other end of conduit 30 secured to disk 15 by screw 17. There are two other flange-like segments at said other end of conduit 30, but they are hidden in FIG. 2 and appear in FIG. 5. Signal electrode 18 is electroplated with layers of copper, nickel and chrome to prevent oxidation. The grounded end sections of the signal electrode rollers are of similar construction but need not be electroplated. Design of the spacer disks is such that grooves 28 (FIG. 1) cut along their circumferences prevent slippage between seed cotton and disks and aid in feeding cotton to the ginnery processes.

The signal electrode 18 can be used either when properly insulated and using the ends of the roller as a ground, or properly insulated and using the chute or hopper 6 as the ground, or properly insulated and using the other rollers 2 as a ground. When using the other rollers 2 as a ground, the seed cotton fed between the rollers acts as a conductor for the current between the rollers.

It is preferred that signal electrode 18 surface area not exceed approximately 155 square inches (7 inches in diameter and 7 inches long). In practice cotton would be in contact with approximately 135° of the feed roller or with 58 square inches. Insulated disks 14 and 15 (FIG. 2) forming spacing between signal and ground should provide a current path length of approximately 0.75 inches.

Figure 4:
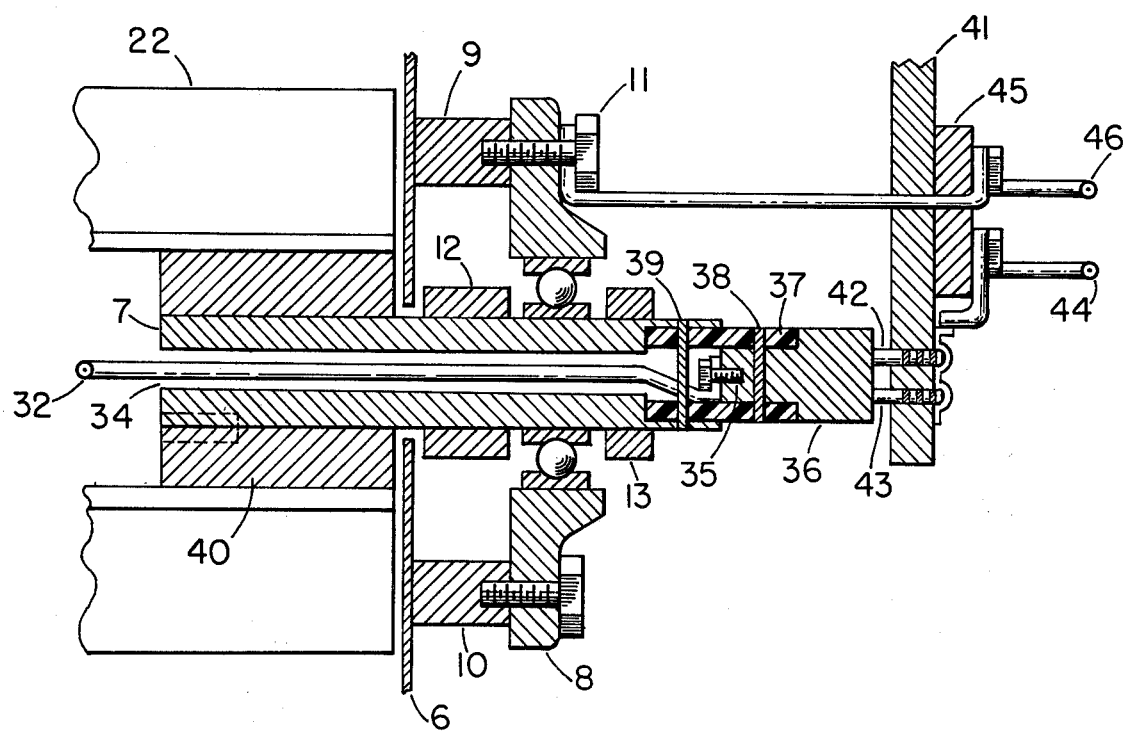
FIG. 4 show the hook up of the signal electrode to the carbon brush assembly outside the hopper wall.

Signal electrode 18 (FIGS. 2 and 3) is electrically connected through conducting screw and nut 31 to shielded cable 32. Shielded cable 32 continues the path from signal electrode 18 to a signal fitting 36 (FIG. 4) at the end of the electrode shaft 7. This cable 32 in its travel passes through a slot 33 (FIG. 2) in disk 15, enters channel 34 (FIG. 4) in the electrode shaft and connects to a terminal screw 35 on signal fitting 36. Signal fitting 36 is insulated from shaft 7 by insulated fitting 37, and pin 39 ties insulated fitting to shaft 7.

Ground 22 is welded to cylindrical block 40 which is keyed to shaft 7. Ground 21 (FIG. 2) and both ends of feed roller 2 (FIG. 1) are connected to their shafts in like manner.

Carbon brush assembly 41 (FIG. 4) collects the current at fitting 36 with one or more brushes 42 and 43 and transmits it via insulated copper wire 44 to terminal strip 45, and then to the electronic measuring circuitry some 20 feet away (not shown).

Although the hopper or chute walls are not a part of the measuring circuit, the ground is electrically connected to the walls and frame of the hopper or chute through the shafts and shaft bearings to insure the ground being at the same potential as the system. In this manner the effects of stray currents are minimized or eliminated. This is guaranteed by cable 46 electrically connecting rolling contact bearing 8 at bolt 11 directly to the measuring circuits.

The measuring and control circuits to be used with this invention are commercially available or are under development by various organizations and are not considered a part of this invention.

We claim:
1. An apparatus for continuously measuring the moisture content in seed cotton being processed through a cotton gin comprising in combination:
  a. a means of initiating an electrical current substantially forming a signal, said signal means comprising in combination the following:
    1. a rotating radial electrode configured to the same configuration as a conventional feed roller in a cotton gin and comprising in combination:
      a. a hollow cylindrical conduit;
      b. a plurality of channel bars affixed equidistantly around the circumference of said conduit; and
      c. a shielded cable affixed to the inside of the conduit;
      d. a means of affixing said shielded cable to the inside of said conduit;
  b. a receiving means communicating with said signal, said receiving means substantially forming a ground;
  c. a means of insulating said signal means from said ground.

2. The apparatus of claim 1 wherein the means of affixing the shielded cable to the conduit is a screw/nut arrangement.

3. The apparatus as defined in claim 1 wherein the insulating means is an inert material of approximately 0.75 inches thickness at the point of constant path for the electrical current.

4. The apparatus as defined in claim 1 wherein the signal means is installed in approximately the center of a conventional feed roller and insulated from the ends of said feed roller substantially forming a feed-roller-electrode, said feed-roller-electrode installed in a cotton ginning system.

5. The apparatus of claim 4 wherein the surface area of the signal electrode is approximately 155 square inches.

6. The apparatus of claim 4 wherein the ends of the said feed-roller-electrode are insulated from the electrode in the center and form the ground.

7. The apparatus as defined in claim 4 wherein the insulating means are inert disks.

8. The apparatus as defined in claim 7 wherein the inert disks are grooved on the outer circumference.

9. The apparatus of claim 4 including a means of housing said feed-roller-electrode.

10. The apparatus of claim 9 wherein the housing means is a chute and hopper walls.

11. The apparatus of claim 10 wherein the chute and hopper walls is insulated from the feed-roller-electrode thus substantially forming a ground.

12. The apparatus of claim 4 wherein the feed-roller-electrode is insulated from a plurality of parallel feed rollers said parallel feed rollers forming a ground.

13. The apparatus of claim 12 wherein the plurality of feed rollers and the feed-roller-electrode are rotated by a system of gears.

14. The apparatus as defined in claim 12 wherein the plurality of feed rollers each comprises in combination:
 a. a cylindrical hollow conduit;
 b. a plurality of channel bars affixed equidistantly around the circumference of the hollow cylindrical conduit of (a);
 c. a shaft afixed to each end of said conduit of (a), said shaft supported by
 d. bearings on each end of said shaft of (c), said bearings affixed to
 e. a housing to support said bearing of (d)
 f. a set of spacers between said housing of (e) and said bearings of (d);
 g. a set of bolts to affix said bearings of (d) to said spacers of (f).

15. The apparatus as defined in claim 12 wherein the feed-roller-electrode comprises in combination:
 a. a cylindrical hollow conduit;
 b. a plurality of channel bars affixed equidistantly around the circumference of said cylindrical conduit;
 c. a hollow shaft affixed at each end of said conduit, said shaft supported by
 d. bearings on each end of said shaft of (c), said bearings affixed to
 e. a housing to support said bearings of (d);
 f. a set of spacers between said housing of (e) and said bearings of (d);
 g. a set of bolts to affix said bearings of (d) to said spacers of (f).

16. The apparatus of claim 15 including a shielded cable installed through said hollow shaft and attached to a bronze fitting which receives an electrical signal, said bronze fitting attached to an inert insulator which is attached to said hollow shaft.

* * * * *